(12) United States Patent
Kamal et al.

(10) Patent No.: US 7,816,119 B2
(45) Date of Patent: Oct. 19, 2010

(54) CHEMOENZYMATIC PROCESS FOR THE STEREOSELECTIVE PREPARATION OF (R)-γ-AMINO-β-HYDROXYBUTYRIC ACID OR (R)-CARNITINE FROM 3,4-DIHYDROXYBUTANENITRILE

(75) Inventors: Ahmed Kamal, Hyderabad (IN); Gollapalli Bhasker Ramesh Khanna, Hyderabad (IN); Tadiparthi Krishnaji, Hyderabad (IN); Rondla Ramu, Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 552 days.

(21) Appl. No.: 11/911,643

(22) PCT Filed: Nov. 29, 2005

(86) PCT No.: PCT/IN2005/000387

§ 371 (c)(1),
(2), (4) Date: Oct. 15, 2007

(87) PCT Pub. No.: WO2006/109322

PCT Pub. Date: Oct. 19, 2006

(65) Prior Publication Data
US 2009/0233337 A1 Sep. 17, 2009

(30) Foreign Application Priority Data
Apr. 15, 2005 (IN) .......................... 963/DEL/2005

(51) Int. Cl.
*C12P 41/00* (2006.01)
(52) U.S. Cl. .................................................... 435/280
(58) Field of Classification Search ....................... None
See application file for complete search history.

(56) References Cited

U.S. PATENT DOCUMENTS

| | | | | |
|---|---|---|---|---|
| 5,248,601 A | * | 9/1993 | Francalanci et al. | 435/128 |
| 5,300,430 A | * | 4/1994 | Shapiro et al. | 435/128 |
| 7,374,926 B2 | * | 5/2008 | Kamal et al. | 435/280 |

FOREIGN PATENT DOCUMENTS

JP 02027995 1/1990

OTHER PUBLICATIONS

Borum, P.R. (1983) "Carnitine," *Ann. Nutr. Rev.* 2:233-259.
Borum (1981) "Possible Carnitine Requirement of the Newborn and the Effect of Genetic Disease on the Carnitine Requirement," *Nutr. Rev.* 39:385-390.
Brehm et al. (1983) "Heterocyclic GABA Agonists. Synthesis and Crystal Structure of (RS)-5-(N-t-butyloxycarbonylaminomethyl)-3-oxoisoxazolidine-2-carboxamide, a Derivative of Dihydromuscimol," *J. Chem. Soc. Perk Trans. I* :1459-1464.
Bremer (1983) "Carnitine—Metabolism and Functions," *Physiol. Rev.* 63:1420-1480.
Chapoy et al. (1980) "Systemic Carnitine Deficiency—A Treatable Inherited Lipid-Storage Disease Presenting as Reye's Syndrome," *New Eng. J. Med.* 303:1389-1394.
De Grandis et al. (Jun. 1980) "Myasthenia Due to Carnitine treatment," *J. Neurol. Sci.* 46:365-371.
Fritz et al. (May 1965) "Carnitine Acetyltransferase," *J. Biol. Chem.* 240(5):2188-2192.
Fritz et al. (1962) "Specificity of Carnitine Action on Fatty cid Oxidation by Heart Muscle," *Am. J. Physiol.* 202:117-121.
Goa et al. (1987) "*I*-Carnitine—A Preliminary Review of its Pharmacokinetics, and its Therapeutic Use in Ischemic Cardiac Disease and Primary and Secondary Carnitine Deficiencies in Relationship to its Role in Fatty Acid Metabolicm," *Drugs* 34:1-24.
Guarnieri et al. (Jul. 1980) "Lipid-Lowering Effect of Carnitine in Chronically Uremic Patients Treated with Maintenance Hemodialysis," *Am. J. Clin. Nutr.* 33:1489-1492.
International Search Report, Corresponding to International Application No. PCT/IN2005/000387, Mailed Apr. 24, 2006.
Jung et al. (1980) "Total Synthesis of ®-G;ycerol Acetonide and the Antiepileptic and Hypotensive Drug (-)-γ-Amino-β-hydroxybutyric Acid (GABOB): Use of Vitamin C as a Chiral Starting Material," *J. Am. Chem. Soc.* 102:6304-6311.
Kasai et al. (Feb. 1992) "An Efficient Synthesis of (r)-Carnitine," *Tetrahedron Lett.* 33(9):1211-1212.
Kolb et al. (Jan. 1993) Short and Practical Synthesis of (R)-(-)-Carnitine and (R)-(-)-γ-Amino-β-hydroxybutyric Acid (GABOB) *Tetrahedron Asymmetry* 4(1):133-141.
Kurono et al. (1977) "Optical Resolution of 4-Amino-3-hydroxybutramide," *Chem. Abstr.* 86:89207u.
Lu et al. (May 1993) "A Simple Total Synthesis of Naturally Occurring Hydroxy-Amino Acids by Enzymatic Kinetic Resolution," *Tetrahedron Asymmetry* 4(5):893-902.
Marconi et al. (1985) "Effects of L-Carnitine Loading on the Aerobic and Anaerobic Performance of Endurance Athletes," *Eur. J. Appl. Physiol.* 54:131-135.

(Continued)

*Primary Examiner*—Sandra E. Saucier
(74) *Attorney, Agent, or Firm*—Greenlee Sullivan P.C.

(57) ABSTRACT

The present invention provides a chemoenzymatic process for the preparation of (R)-GABOB and (R)-carnitine employing lipase-mediated resolution of 3-hydroxy-4-tosyloxybutanenitrile as the key step. The drawing accompanying this specification represents the preparation of racemic 3-hydroxy-4-tosyloxybutanenitrile, its lipase-mediated kinetic resolution and its successful application in the preparation of (R)-GABOB and (R)-carnitine.

11 Claims, 1 Drawing Sheet

OTHER PUBLICATIONS

McGarry et al. (1980) "Regulation of Hepatic Fatty Acid Oxidation and Ketone Body Production," *Ann. Rev. Biochem.* 49:395-420.

Naidu et al. (Dec. 2000) "Microbial and Enzymatic Production of L-Carnitine," *Bioprocess Eng.* 23(6):627-635.

Otsuka et al. (1971) "Measurement of γ-Aminobutyric Acid in Isolated Nerve Cells of Cat Central Nervous System," *J. Neurochem.* 18(2):287-295.

Otsuka et al. (1972) "Application of Enzymatic Cycling to the Measurement of Gamma-Aminobutyric Acid in Single Neurons of the Mammalian Central Nervous System," In; *Advances in Biochemical Psychopharmacology*, vol. 6, Raven, New York pp. 61-74.

Takano et al. (1987) "Practical Synthesis of (R)-γ-Amino-β-hydroxybutanoic Acid (GABOB) from (R)-epichlorohydrin," *Tetrahedron Lett.* 28(16):1783-1784.

Thomsen et al. (Feb. 1979) "Improved Pacing Tolerace of the Ischemic Human Myocardium after Administration of Carnitine," *Am. J. Cardiol.* 43(2):300-306.

Voeffray et al. (1987) "L-Carnitine. Novel Synthesis and Determination of the Optical Purity," *Helvetica Chimica Acta* 70(8):2058-2064.

Wang et al. (1999) "Synthesis Routes to L-Carnitine and L-Gamma-Amino-Beta-Hydroxbutyric Acids from (S)-2-Hydroxybutyrolactone by Functional Group Priority Switching," *Tetrahedron Asymmetry* 10(10):1895-1901.

Wong et al. (1985) "Enzymatic vs. Fermentative Synthesis: Thermostable Glucose Dehydrogenase Catalyzed Regeneration of NAD(P)H for use in Enzymatic Synthesis," *J. Am. Chem. Soc.* 107(13):4028-4031.

* cited by examiner

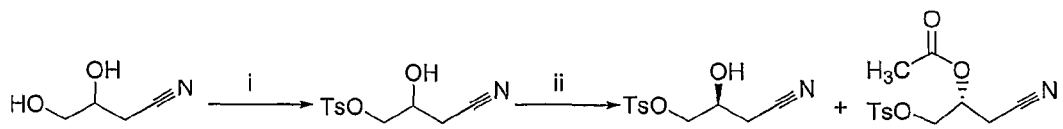
Reagents and conditions : i. Bu$_2$SnO, TsCl, Et$_3$N, DCM. ii. PS-D, vinyl acetate, diisopropyl ether, rt.
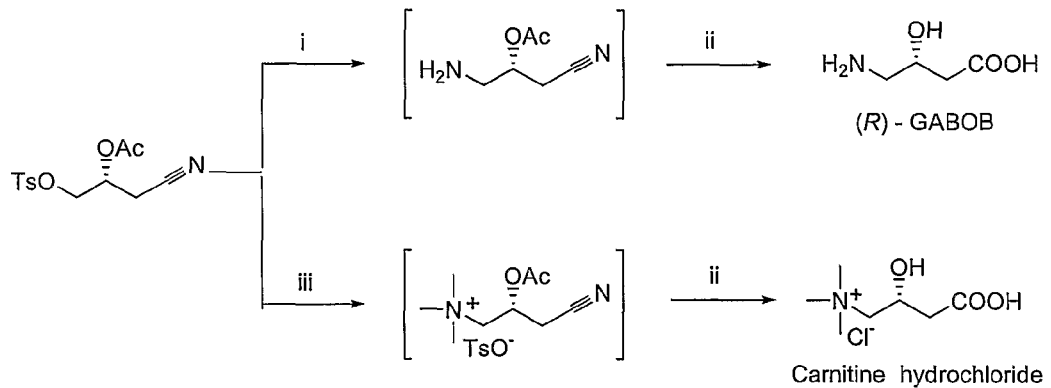
Reagents and conditions : i. aqueous ammonia, EtOH reflux; ii. dil. HCl reflux; iii. aqueous trimethylamine EtOH reflux.

CHEMOENZYMATIC PROCESS FOR THE STEREOSELECTIVE PREPARATION OF (R)-γ-AMINO-β-HYDROXYBUTYRIC ACID OR (R)-CARNITINE FROM 3,4-DIHYDROXYBUTANENITRILE

CROSS-REFERENCE TO RELATED APPLICATIONS

This application is a national stage application under 35 U.S.C. §371 of PCT/IN2005/000387, filed Nov. 29, 2005 which takes priority from Indian Patent Application 963/Del/2005 filed Apr. 15, 2005, both of which are incorporated by reference in their entirety herein.

The present invention relates to a chemoenzymatic process for the stereoselective preparation of (R)-γ-amino-β-hydroxybutyric acid ((R)-GABOB) and (R)-carnitine.

More particularly, the present invention particularly relates to a chemoenzymatic process for the stereoselective preparation of (R)-GABOB and (R)-carnitine employing optically pure 3-acetyloxy-4-tosyloxybutanenitrile obtained by lipase-mediated kinetic resolution of its racemate. (R)-GABOB is a compound of great pharmacological importance because of its biological function as a neuromodulator in the mammalian central nervous system (Otsuka, M.; Obata, K.; Miyata, Y.; Yaneka, Y. *J. Neurochem.* 1971, 18, 287; Otsuka, M.; Obata, K.; Miyata, Y. Advances in Biochemical Psychopharmacology Raven: New York, 1972, Vol 6. pp 61). It is known to function as an agonist of gamma-aminobutyric acid (GABA) and has been found to be a remarkable antiepileptic and hypotensive drug (Brehm, L.; Jacobsen, P.; Johansen, J. S.; Krogsgaard-Larsen, P. *J. Chem. Soc. Perkin Trans I* 1983, 1459). It has also been demonstrated to be effective in managing a variety of clinical conditions including schizophrenia and other character based illnesses (Chapoy, P. R.; Angelini, C; Brown, W. J.; Stiff, J. E.; Shug, A. L.; Cederbaum, S. D. *N. Engl. J. Med.* 1980, 303, 1389; Takano, S.; Yanase, M.; Sekiguchi, Y.; Ogasawara, K. *Tetrahedron Lett.* 1987, 28, 1783), epilepsy and other illnesses that result in severe convulsions. Its use for the correction of some clinical condition observed in children has also been explored.

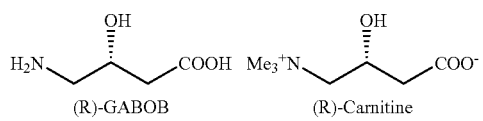

(R)-GABOB             (R)-Carnitine

Carnitine is a vitamin like substance and plays an important role in converting stored body fat into energy. Its primary physiological function is to transport long chain fatty acids through the mitochondrial membrane into the cellular compartments for oxidation where these fats can be converted into energy (Fritz, I. B.; Kaplan, E.; Yu, K. T. N. *Am. J. Physiol.* 1962, 202, 117; Bremer, J. *Physiol. Rev.* 1983, 63, 1420; Brown, W. J.; Stiff, J. E.; Shug, A. L.; Cederbaum, S. D. *N. Engl. J. Med.* 1980, 303, 1389; McGarry, J. D.; Foster, D. W. *Ann. Rev. Biochem.* 1980, 49, 395). As cells derive energy in this process carnitine is important for cellular energitics and it has been used in therapy as a stimulator of fatty acid degradation. In the absence of carnitine many fats cannot be burned and accumulate within the cell and in the blood stream as fats and triglycerides (high risk factor for heart patients) in this way it has been proved to be beneficial to heart patients (Thomsen, J. H.; Sug, A. L.; Yap, V. U.; Patel, A. K.; Karras, T. J.; De Felice, S. L. *Amer. J. Cardiol.* 1979, 33, 300). There are several medical indications for which carnitine has been prescribed these include its usefulness as a pharmaceutical for hemodialysis (hypolipidemic agent), heart diseases and myopathic deficiencies etc (Goa, K. L.; Brogden, R. N. *Drugs* 1987, 34, 1.; Guarnieri, G.; Ranieri, F.; Toigo, G.; Vasile, A.; Cinam, M.; Rizzili, V.; Morachiello, M.; Campanacci. L. *Am. J. Clin. Nutr.* 1980, 33, 1489; Chapoy, P. R.; Angelini, C; Brown, W. J.; Stiff, J. E.; Shug, A. L.; Cederbaum, S. D. *N. Engl. J. Med.* 1980, 303, 1389; Borum, P. R. *Nutr. Rev.* 1981, 39, 385). It has an important role in the energy metabolism and is involved in regulating blood lipids, it is an efficient drug to improve the myocardial function and also used in sport medicine, infant nutrition and also as an antiobesity agent (Marconi, C; Sassi, G.; Carpinelli, A.; Cerretelli, P. *Eur. J. Appl. Physiol.* 1985, 54, 131; Borum, P. R. *Ann. Nutr. Rev.* 1983, 3, 233).

The R-form of GABOB is shown to have greater biological activity than its S-enantiomer (Kurano; Masayasu; Miyaruto; Shigetoshi; Shigeoka; Satoshi; Mori; Akitane. Japanese Patent 1976; *Chem. Abstr.* 1977, 86, 89207u; Otsuka, M.; Obata, K.; Miyata, Y.; Yaneka, Y. *J. Neurochem.* 1971, 18, 287; Otsuka, M.; Miyata, Y. Advances in Biochemical Psychopharmacology, Raven, New York, 1972, Vol 6, pp 61; Kurono, M.; Miyamoto, S.; Shigeoka, S.; Mori, A. Japan, Kokai 76,100,026; Chem. Abstr. 1977, 86, 89207u). Moreover, the R-isomer of GABOB serves as a precursor for (R)-carnitine. The discovery of the adverse effects of (S)-carnitine (Wong, C. H.; Drueckhammer, D. G.; Sweers, N. M. *J. Am. Chem. Soc.* 1985, 107, 4028; DeGrandis, D.; Mezzina, C; Fiaschi, A.; Pinelli, P.; Bazzato, G.; Morachiello, M. *J. Neurol. Sci.* 1980, 46, 365) and the questionable effectiveness of the racemic mixture in angina pectoris coupled with the recent growing interest in therapeutic application of carnitine has prompted their preparation in only (R)-form. Moreover, the (S)-enantiomer of carnitine acts as a competitive inhibitor of (R)-carnitine acyl transferase (Fritz, I. B.; Schultz, S. K. *J. Biol. Chem.* 1965, 240, 2188) resulting in the depletion of carnitine level in heart tissues. Hence, their preparation and use in enantiomerically pure form (R-form) is highly desirable.

In spite of the simple structure of GABOB and carnitine a numerous number of methods for their enantioselective preparation are described in the literature (Wang, G.; Hollingsworth, R. I. *Tetrahedron: Asymmetry* 1999, 10, 1895 and references cited therein). They have been prepared by optical resolution, asymmetric synthesis from natural products, catalytic asymmetric synthesis and by employing enzymes in the key enantioselective step. Earlier approaches reported in the literature have either long reaction sequences there by reducing the overall yield or have employed chiral starting material not in the chiral pool or have obtained the target compounds in low enantioselectivity. In view of the high biological importance associated with these compounds a more facile, efficient and cost effective approach has been investigated. Both carnitine and GABOB have four-carbon chain in their basic structural skeleton and retrosynthetic strategy reveals that enantiomerically pure 3-hydroxy-4-tosyloxybutanenitrile or 3-acetyloxy-4-tosyloxybutanenitrile can be excellent chiral building blocks for the synthesis of target molecules.

The main objective of the present invention is to provide a chemoenzymatic process for the stereoselective preparation of both 3-acetyloxy-4-tosyloxybutanenitrile, which provides a shortest path for the synthesis of both (R)-GABOB and (R)-carnitine and in high enantiomeric excess.

The approximate calculated yields of (R)-GABOB and (R)-carnitine as described in prior art publications are tabulated below:

| S. No. | References | Yield % | No. of steps |
|---|---|---|---|
| 1. | Present invention | 25 | 3 |
| 2. | Lu, Y.; Miet, C.; Kunesch, N.; Poisson, J. E. Tetrahedron: 1993, 4, 893 | 29 | 5 |
| 3. | Kasai, N.; Sakaguvhi, K. Tetrahedron Letter, 1992, 33, 1211 | 9 | 5 |
| 4. | Voeffray, R.; Perlberger, J-C.; Tenud, L. Helv. Chimica Acta, 1987, 70, 2058 | 16 | 5 |
| 5. | Wang, G.; Hollingsworth, R. I.; Tetrahedron: Asymmetry 1999, 10, 1895 | 67 | 6 |
| 6. | Jung, M. E.; Shaw, T. J.; J.Am.Chem.Soc. 1980, 102, 6302 | 10 | 9 |
| 7. | Kolb, H. C.; Bennani, Y. L.; Sharpless, K. B.; Tetrahedron: Assymetry, 1993, 4, 133 | 19 | 5 |

STATEMENT OF INVENTION

The present invention provides a chemoenzymatic process for the preparation of (R)-GABOB and (R)-carnitine employing lipase-mediated resolution of 3-hydroxy-4-tosyloxybutanenitrile as the key step. The drawing accompanying this specification represents the preparation of racemic 3-hydroxy-4-tosyloxybutanenitrile, its lipase-mediated kinetic resolution and its successful application in the preparation of (R)-GABOB and (R)-carnitine.

The enzyme lipase used in chemoenzymatic process for the preparation of (R)-GABOB and (R)-carnitine were procured from commercially available sources such as *Pseudomonas cepacia* lipase and *Pseudomonas fluorescens* from Amano Pharmaceutical Co., Japan; *Candida rugosa* lipase (CRL) from Sigma, USA; *Candida antartica* lipase immobilized in Sol-Gel-AK on sintered glass (CAL B) from Fluka, Germany.

Accordingly the present invention provides a chemoenzymatic process for the stereoselective preparation of both (R)-GABOB and (R)-carnitine, the said process comprising the steps of:

i) tosylating 3,4-dihydroxybutanenitrile by reacting 3,4-dihydroxybutanenitrile with dibutyltinoxide, p-toluene sulphonyl chloride and a base in the presence of an organic solvent, at a temperature ranging between 25-30° C. under nitrogen atmosphere, for a period of 1-3 hrs., adding water to the above said reaction mixture and separating the organic layer, followed by concentration and purification by known method to obtain the racemic 3-hydroxy-4-tosyloxybutanenitrile, ii) resoluting racemic 3-hydroxy-4-tosyloxybutanenitrile with an acetylating agent in the presence of lipase in an organic solvent, at a temperature of 25-30° C. followed by filtration and washing to obtain (R)-3-hydroxy-4-tosyloxybutanenitrile, iii) converting (R)-3-hydroxy-4-tosyloxybutanenitrile (R)-GABOB and (R)-carnitine by reacting it with a base in an organic solvent under reflux for an overnight period followed by evaporation, adding concentrated HCl to the resultant residue and heating to a temperature in the range of 60-90° C., for a period of about 6 hr followed by evaporation and purification by known method to obtain the desired product.

In an embodiment of the present invention the base used in step i) is selected from the group consisting of pyridine, trimethyl amine, DABCO and potassium t-butoxide.

In another embodiment of the present invention the organic solvent used in step i) is selected from the group consisting of benzene, toluene, dichloromethane, chloroform, tetrahydrofuran and N,N-dimethylformamide.

In yet another embodiment of the present invention the acetylating agent used is selected from vinyl acetae and isopropenyl acetate.

In yet another embodiment the lipase used is selected from the group consisting of *Pseudomonas cepacia* lipase immobilized on modified ceramic particles (PS-C), *Pseudomonas cepacia* lipase immobilized on diatomite (PS-D), *Pseudomonas cepacia* (PS), *Pseudomonas fluorescens* lipase immobilized on Sol-Gel-AK on sintered glass (P), *Pseudomonas fluorescens* lipase (AK), immobilized lipase from *Mucor meihei* (Lipozyme), *Candida rugosa* lipase (AYS), *Candida rugosa* lipase (CRL) and *Candida antartica* lipase immobilized in Sol-Gel-AK on sintered glass (CAL B)

In yet another embodiment the organic solvent used in step ii) is selected from the group consisting of diisopropylether, hexane, diethyl ether, toluene, chloroform, acetone, tetrahydrofuran and dioxane In yet another embodiment the base used in step iii) is selected from aqueous ammonia and aqueous trimethyl amine.

In yet another embodiment the organic solvent used in step iii) is selected from methanol and ethanol.

In still another embodiment the enantiomeric excess of kinetic resolution is >99%.

The following examples are given by way of illustration and they should not be construed to limit the scope of the present invention.

EXAMPLE 1

(±-3-Hydroxy-4-tosyloxybutanenitrile: To 3,4-dihydroxy butanenitrile (10:10 g, 100.00 mmol) dispersed in 250 mL of DCM was added dibutyltinoxide (4.98 g, 20.00 mmol), Et$_3$N (25.25 g, 250.00 mmol) and p-toluenesulphonyl chloride (20.95 g, 110.00 mmol) at room temperature and under N$_2$. The resultant reaction mixture was stirred at room temperature and the progress of the reaction was monitored by TLC. After completion of the reaction (2 h), 150 mL, of water was added and organic layer was separated. The aqueous layer was extracted with DCM (3×150 mL) and the combined organic layers were dried over anhydrous Na$_2$SO$_4$, concentrated and the residue was purified by column chromatography employing EtOAc-hexane (35:65) as eluent to afford pure 3-hydroxy-4-(4-methylphenylsulphonyloxy)butanenitrile in 65% yield. IR (Neat) 3474, 3059, 2933, 2902, 2220, 1584, 1349, 1169, 1098, 996 cm$^{-1}$; $^1$HNMR (300 MHz, CDCl$_3$) δ 2.48 (s, 3H), 2.52-2.67 (m, 2H), 4.06 (d, 2H, J=5.4 Hz), 4.15-4.22 (m, 1H), 7.38 (d, 2H, J=8.3 Hz), 7.80 (d, 2H, J=8.3 Hz); Mass (EI) 255 (M$^+$), 173, 155, 139, 122, 91.

EXAMPLE 2

(+−3-Acetyloxy-4-tosyloxybutanenitrile: To 3-hydroxy-4-tosyloxybutanenitrile (5.00 mmol) under N$_2$ was added acetic anhydride (20.00 mmol) and pyridine (5.50 mmol) and the resultant mixture was stirred at room temperature overnight. After completion of the reaction (TLC) the reaction mixture was diluted with ethyl acetate (25 mL) and treated with 1N HCl (20 mL). The organic layer was separated, washed with brine and dried over anhydrous Na$_2$SO$_4$. The solvent was evaporated and the residue was purified by column chromatography employing EtOAc-hexane (25:75) as eluent to afford the required 3-acetyloxy-4-tosyloxybutanenitrile in nearly quantitative yield, $^1$HNMR (200 MHz, CDCl$_3$) δ 2.09 (s, 3H), 2.49 (s, 3H), 2.75 (d, 2H, J=5.9 Hz), 3.67-4.18 (m, 2H), 5.09-5.15 (m, 1H), 7.38 (d, 2H, J=8.0 Hz), 7.79 (d, 2H, J=8.0 Hz): Mass (EI) 297 (M+), 255, 185, 172, 155, 139, 91; yield 93%.

EXAMPLE 3

Procedure for resolution of 3-hydroxy-4-tosyloxybutanenitrile: To a solution of 3-hydroxy-4-tosyloxybutanenitrile (1.50 g) in diisopropyl ether (150 mL) were successively added lipase (1.20 g) and vinyl acetate (6 equivalents) and shaken at room temperature in orbital shaker. After about 50% completion of the reaction as indicated by the HPLC analysis the reaction mixture was filtered and residue was washed thrice with diisopropyl ether. The combined organic layers were evaporated under reduced pressure and purification was accomplished by column chromatography employing EtOAc-hexane (30:70) as eluent to afford the corresponding (R)-acetate followed by (S)-alcohol.

(S)-3-Hydroxy-4-tosyloxybutanenitrile: $[\alpha]^{26}_D$=−14.5 (c 1.45, EtOH); lit. $[\alpha]^{25}_D$=−14.2 (c 1.72, EtOH); IR, NMR and Mass spectral data are identical to racemic 3-hydroy-4-tosyloxybutanenitrile; Yield 44%.

(R)-3-Acetyloxy-4-(4-methylphenylsulphonyloxy)butanenitrile: $[\alpha]^{28}_D$=+22.6 (c 1.0, $CHCl_3$); NMR and Mass spectral data are identical to 3-acetyloxy-4-tosyloxybutanenitrile; Yield 46%.

EXAMPLE 4

Chiral HPLC analysis: HPLC analysis was performed on an instrument that consisted of a Shimadzu LC-10AT system controller with a SPD-10A fixed wavelength UV monitor as a detector. Analysis were performed by employing chiral column (chiralpak ADH, Daicel) with hexane:isopropanol (93:07) as the mobile phase at a flow rate of 0.7 mL/min and monitored at UV-254 nm. Racemic acetate was prepared as described in example 2 as an authentic sample for comparison on HPLC.

EXAMPLE 5

(R)-GABOB: To a solution of (R)-3-acetyloxy-4-tosyloxybutanenitrile (4.07 g, 13.70 mmol) in ethanol (40 mL,) was added excess aq.$NH_3$, refluxed overnight and the solvents in the reaction mixture were evaporated. To the resulting residue was added conc. HCl and heated to 80° C. for 6 h. After evaporation of the solvent the residue containing crude (R)-GABOB was purified over an on exchange column, chromatography (Amberlite IR-120$H^{-1}$). The column was first eluted with water until the fractions were neutral and later with 10% $NH_4OH$. Evaporation of the basic fractions gave thick oil, which was dissolved in minimum amount of water and absolute ethanol was added to provide (R)-GABOB as a white solid (84%). Recrystallization of the (R)-GABOB from water-ethanol provided pure (R)-GABOB as white crystals (73%) yield, m.p. 211-213° C.; $[\alpha]_D$=−20.7 (c 1.0, $H_2O$); $^1$HNMR (200 MHz, $D_2O$) δ 2.43 (d, 2H, J=5.9 Hz), 2.95 (dd, 1H, $J_1$=9.66 Hz, $J_2$=13.38 Hz), 3.18 (dd, 1H, $J_1$=3.72 Hz, $J_2$=13.38 Hz), 4.10-4.30 (m, 1H); $^{13}$CNMR (50 MHz, $D_2O$) δ 42.3, 44.0, 65.5, 178.5; Mass (EI) 118 (M+-H), 74, 60, 43.

EXAMPLE 6

(R)-Carnitine: To a solution of (R)-3-acetyloxy-4-tosyloxybutanenitrile (4.07 g, 13.70 mmol) in ethanol (40 mL) was added excess aq., trimethyl amine, refluxed overnight and the solvents in the reaction mixture were evaporated. To the resulting residue was added conc. HCl and heated to 80° C. for 6 h after evaporation of the solvent the residue containing crude (R)-carnitine was purified over an on exchange column, chromatography (Amberlite IR-120 W). The column was first eluted with water until the fractions were neutral and later with 10% $NH_4OH$. Evaporation of the basic fractions gave a thick oil, which was again acidified with conc. HCl. Evaporation of the solvent afforded carnitine as hydrochloride salt. Trituration with isopropanol afforded colourless solid of (R)-carnitine hydrochloride, m.p. 44-146° C.; $[\alpha]^{30}_D$=−22.4 (c 1.5, $H_2O$); $^1$HNMR (200, $D_2O$) δ 2.60-2.70 (m, 2H), 3.24 (s, 9H); 3.48-3.55 (m, 2H); 4.60-4.75 (m, 1H); $^{13}$CNMR (75 MHz, $D_2O$) [[n]] 39.9, 54.2, 62.8, 69.7, 173.8; Mass (FAB) 162 (M++1).

The Advantages of the Present Invention are:

β-Hydroxy nitriles or vicinal cyanohydrins are important and versatile compounds in organic synthesis as these hydroxy nitriles in optically pure form provide a number of opportunities for synthetic manipulations leading to a wide range of chiral synthesis like amino alcohols, hydroxy amides, hydroxy acids, hydroxy esters etc.

The high functionality of the 3-hydroxy4-tosyloxybutanenitrile (tosyloxy group, hydroxyl group, nitrile group) makes it a very useful intermediate for synthesis of a variety of optically pure compounds of biological importance.

Also, the intermediates obtained in this process are of at most optical purity, which is essential for the preparation of target biologically important compounds.

In this process the target compounds have been obtained in a simple, facile and through a shortest route.

We claim:

1. A chemoenzymatic process for the stereoselective preparation of (R)-γ-amino-β-hydroxybutyric acid ((R)-GABOB) or (R)-carnitine comprising:
   i) forming a reaction mixture of 3,4-dihydroxybutanenitrile with dibutyltin oxide, p-toluenesulfonyl chloride and a base in an organic solvent,
   maintaining the reaction mixture at a temperature between 25-30° C. under a nitrogen atmosphere for 1-3 hours, thereby tosylating the 3,4-dihydroxybutanenitrile,
   adding water to the reaction mixture to form an organic layer and a water layer,
   separating the organic layer,
   concentrating and purifying the racemic 3-hydroxy-4-tosylbutanenitrile;
   ii) resolving the racemic 3-hydroxy-4-tosyloxybutanenitrile by reacting it with an acylating agent in an organic solvent catalyzed by a lipase at a temperature of 25-30° C.,
   filtering and washing the resolved (R)-3-hydroxy-4-tosyloxybutanenitrile;
   iii) reacting the resolved (R)-3-hydroxy-4-tosyloxybutanenitrile with a base in an organic solvent under reflux,
   evaporating the solvent to produce a residue,
   adding concentrated HCl to the residue,
   heating to a temperature of 60-90° C. for about 6 hours,
   evaporating and purifying to obtain (R)-GABOB or (R)-carnitine.

2. A process as claimed in claim 1, wherein the base used in step i) is selected from the group consisting of pyridine, trimethyl amine, DABCO and potassium t-butoxide.

3. A process as claimed in claim 1, wherein the organic solvent used in step i) is selected from the group consisting of benzene, toluene, dichloromethane, chloroform, tetrahydrofuran and N,N-dimethylformamide.

4. A process as claimed in claim 1, wherein the acetylating agent used is selected from vinyl acetate and isopropenyl acetate.

5. A process as claimed in claim 1, wherein the lipase used in step ii) is a lipase selected from the group consisting of lipase from *Pseudomonas cepacia*, lipase from *Pseudomonas cepacia* immobilized on diatomite, lipase from *Pseudomonas cepacia* immobilized on modified ceramic particles, lipase from *Pseudomonas fluorescens*, lipase from *Pseudomonas fluorescens* immobilized in Sol-Gel-AK on sintered glass, immobilized lipase from *Mucor miehei*, lipase from *Candida rugosa* and lipase from *Candida antarctica* immobilized in Sol-Gel-AK on sintered glass.

6. A process as claimed in claim 1, wherein the organic solvent used in step ii) is selected from the group consisting of diisopropylether, hexane, diethyl ether, toluene, chloroform, acetone, tetrahydrofuran and dioxine.

7. A process as claimed in claim 1, wherein the base used in step iii) is selected from aqueous ammonia and aqueous trimethyl amine.

8. A process as claimed in claim 1, wherein the organic solvent used in step iii) is selected from methanol and ethanol.

9. A process as claimed in claim 1, wherein the enantiomeric excess of kinetic; resolution is >99%.

10. A process as claimed in claim 7, wherein the base used in step iii) is aqueous ammonia and (R)-GABOB is obtained.

11. A process as claimed in claim 7, wherein the base used in step iii) is aqueous trimethyl amine and (R)-carnitine is obtained.

* * * * *